July 10, 1962 A. MEILLAND Plant Pat. 2,155
ROSE PLANT
Filed Sept. 18, 1961
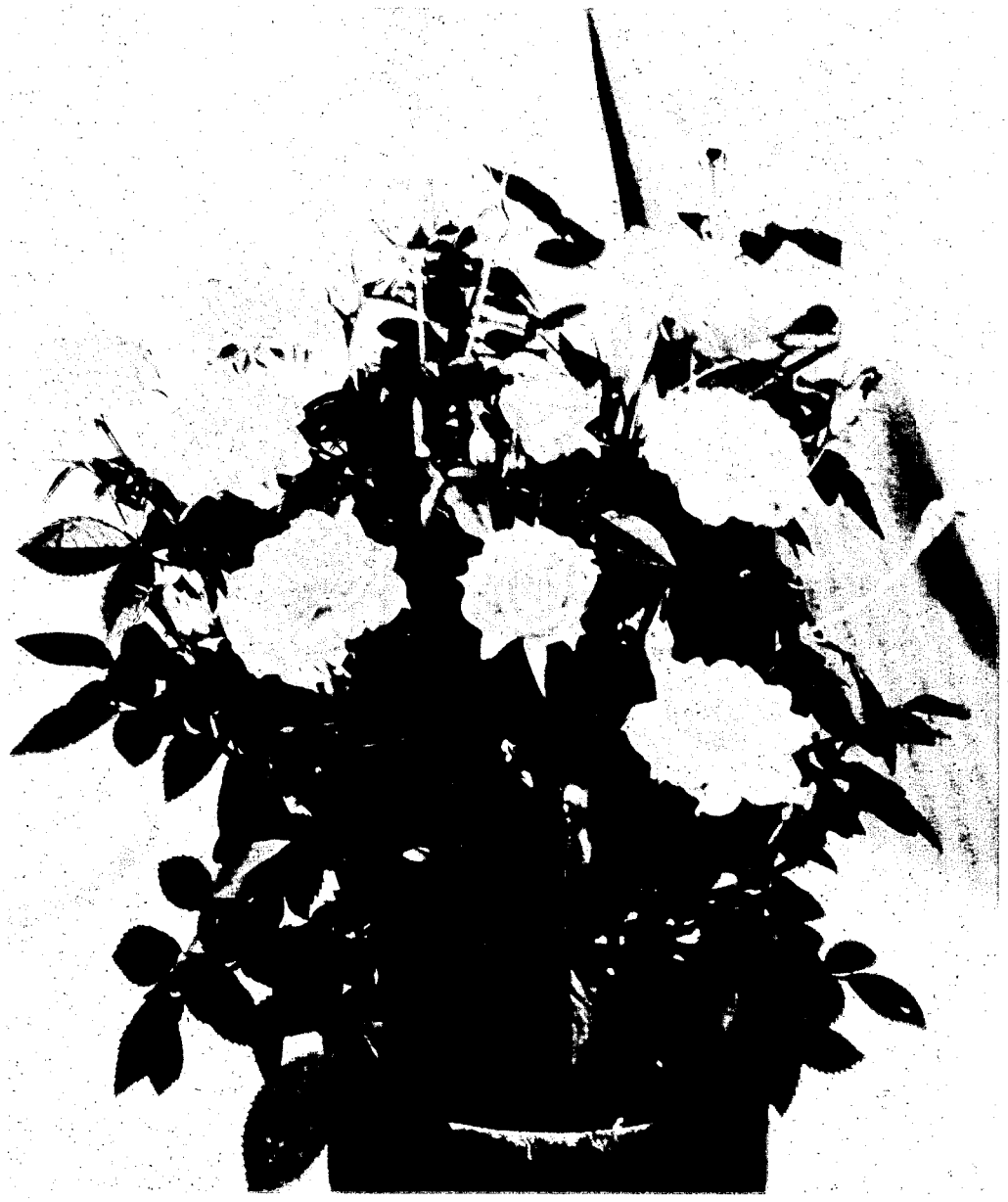
INVENTOR
Alain Meilland
BY Robb & Robb
ATTORNEYS United States Patent Office Plant Pat. 2,155
Patented July 10, 1962

2,155
ROSE PLANT

Alain Meilland, Cap d'Antibes, Alpes Maritimes, France, assignor to The Conard-Pyle Company, West Grove, Pa., a corporation of Pennsylvania Filed Sept. 18, 1961, Ser. No. 139,019
1 Claim. (Cl. 47—61)

The present invention relates to a new and distinct variety of Rose Plant of the miniature class, which was originated by me by crossing an unnamed and unpatented floribunda seedling derived from a cross of "Moulin Rouge" (U.S. Plant Patent No. 1,298) × "Fashion" (U.S. Plant Patent No. 789), with an unnamed and unpatented miniature seedling derived from a cross of "Perla de Montserrat" (unpatented) × "Perla d'Alcanada" (unpatented).

The primary objective of this breeding was to produce a new miniature rose variety which bears flowers of orange-scarlet coloration of the unnamed floribunda seedling parent referred to above, combined with a dwarf habit and good hardiness corresponding to the other parent. This objective was fully achieved, along with other desirable improvements, as evidenced by the following unique combination of characteristics which are outstanding in the new variety and which distinguish it from its parents, as well as from all other varieties of which I am aware:

(1) A compact and dwarf habit of growth;
(2) Good hardiness;
(3) Perfect miniature form of the flowers which average about 1 inch in diameter; and
(4) A Blood Red color tonality of the flowers, which represents a new color break in roses of the miniature class.

Asexual reproduction of the new variety by both cuttings and budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; dwarf; outdoor; seedling; for garden decoration.
Class: Miniature.
Breeding: Seedling.
*Seed parent.*—An unnamed seedling of "Moulin Rouge" × "Fashion."
*Pollen parent.*—An unnamed seedling of "Perla de Montserrat" × "Perla d'Alcanada."
Propagation: Holds its distinguishing characteristics through succeeding propagations by cuttings and by budding.

*Flower*

Locality where grown and observed: West Grove, Pennsylvania, U.S.A.
Flowers borne: Often singly, but usually several to stem; in irregular cluster; on short stems of normal strength.
Quantity of bloom: Free, outdoors.
Continuity: Continuous.

Fragrance: Slight. Nature—tea.
Bud:
*Peduncle.*—Short; slender; erect; stiff; almost smooth; with few green hairs. Color—near Scheeles Green, Plate 860.
*Before calyx breaks.*—Size—small. Form—short; pointed; ovoid; with a conspicuous neck; with foliaceous appendages on the surface of the bud; with bristle-like foliaceous parts extending beyond the tip of the bud equal to ¼ or more of its length.
*As calyx breaks.*—Color—slightly darker than Cherry, Plate 722.
*As first petal opens.*—Size—very small. Form—short; nearly globular. Colour: outside—Cardinal Red, Plate 822, with basal area of petal Sap Green, Plate 62/3; inside—Blood Red, Plate 820, with basal area of petal Chartreuse Green, Plate 663/1.
*Opening.*—Opens up well.
Bloom:
*Size (when fully open).*—Very small; from 1 inch to 1¼ inches.
*Petalage.*—Very double; from 55 to 60 petals; arranged regularly.
*Form.*—Cupped at first, but becoming almost globular; petals being at first loosely rolled outward, and remaining rolled outward at maturity.
Petals: Leathery; with inside velvety and outside satiny.
*Shape.* — Outer — obovate. Intermediate — obovate. Inner—lanceolate.

This description of a newly opened flower was made from a rose grown in a greenhouse during the month of July at West Grove, Pennsylvania, U.S.A.:

*Color.*—Outer petal: outside surface—Cardinal Red, Plate 822, with basal area of petal Sap Green, Plate 62/3; inside surface—Blood Red, Plate 820, becoming Sap Green, Plate 62/3 at base of petal. Intermediate petal: outside surface—Cardinal Red, Plate 822, with basal area of petal Sap Green, Plate 62/3; inside surface—Blood Red, Plate 820, with basal area of petal Sap Green, Plate 62/3. Inner petal: outside surface—Cardinal Red, Plate 822, with basal area of petal Sap Green, Plate 62/3; inside surface—Blood Red, Plate 820, with basal area of petal Sap Green, Plate 62/3.

This description was made from a rose that was open for 3 days in a greenhouse during the month of July at West Grove, Pennsylvania, U.S.A.:

*Color.*—Outer petal: outside surface—Cardinal Red, Plate 822/3, with basal quarter of petal Sap Green, Plate 62/3; inside surface—Blood Red, Plate 820/2 over outer area of petal, becoming tinted with Crimson, Plate 22/2, with basal quarter of petal Chartreuse Green, Plate 663/3. Inner petal: outside surface—Cardinal Red, Plate 822/3, with basal quarter of petal Sap Green, Plate 62/3; inside surface—Blood Red, Plate 820/3 covering outer half of petal, becoming tinted with Crimson, Plate 22/2, with basal quarter of petal Sap Green, Plate 62/3.
*General color effect.*—Newly opened flower—Blood Red, Plate 820. 3-days open—Blood Red, Plate 820/3.
*Behavior.*—Drop off cleanly.
*Flower longevity.*—On bush in garden—5 or 6 days during August. Cut roses grown in greenhouse and kept at living room temperatures—5 days during August.

*Reproductive Organs*

Stamens: Medium number; arranged irregularly about pistils.

Filaments: Few; short; most with anthers. Color—Uranium Green, Plate 63/3.

Anthers: Open at various times; very small; seldom an anther fused with a petaloid. Color—Aureolin, Plate 3.

Pollen: Moderate quantity. Color—gold.

Pistils: Few.

Styles: Uneven; very short; thin; loosely bunched.

Stigma: Color—white-yellow.

Ovaries: Some protruding from receptacle.

Hips: None observed.

Sepals: Permanent; very short; spear-shaped.

Seeds: None observed.

*Plant*

Foliage:

*Leaves.*—Compound of 5 or 7 leaflets; normal abundance; very small; leathery.

*Leaflets.*—Shape—oval, with apex acute. Base—usually acute. Margin—simply serrate.

*Color.*—Mature: upper surface—near Spinach Green, Plate 0960; under surface—slightly lighter than Spinach Green, Plate 0960/3. Young: upper surface—Spinach Green, Plate 0960/1, with a thin margin of Maroon, Plate 1030; under surface—Lettuce Green, Plate 861 on veins, often lightly suffused with Maroon, Plate 1030.

*Rachis (the supporting stem of the compound leaf).*—Light. Upper side—grooved; hairy. Under side—sparsely prickly.

*Stipules.*—Very short; very narrow; with short points turning out at an angle of 45°.

*Disease resistance.*—Comparable to that of the average variety grown under the same cultural conditions at West Grove, Pennsylvania, U.S.A.

Growth:

*Habit.*—Dwarf; bushy; much-branched.

*Growth.*—Free.

*Canes.*—Light.

*Main stems.*—Bright. Color—Spinach Green, Plate 0960/1. Prickles—several; color—near Garnet Brown, Plate 00918/3. Hairs—none.

*Branches.*—Color—Scheeles Green, Plate 860. Prickles—several; color—near Garnet Brown, Plate 00918/3 at base, with tips Fern Green, Plate 0862/3. Hairs—none.

*New shoots.*—Color—Scheeles Green, Plate 860, often overlaid very lightly with Garnet Brown, Plate 00918/3. Prickles—several; color—near Garnet Brown, Plate 00918/3. Hairs—none.

I claim:

A new and distinct variety of rose plant of the miniature class, substantially as herein shown and described, characterized particularly as to novelty by the unique combination of a compact and dwarf habit of growth, good hardiness, a perfect miniature form of the flowers, and a Blood Red general color tonality of the flowers.

No references cited.